US005649950A

United States Patent [19]

Bourne et al.

[11] Patent Number: 5,649,950
[45] Date of Patent: Jul. 22, 1997

[54] SYSTEM FOR THE PERCUTANEOUS TRANSLUMINAL FRONT-END LOADING DELIVERY AND RETRIEVAL OF A PROSTHETIC OCCLUDER

[75] Inventors: George Bourne, Libertyville, Ill.; Randall W. Davis, N. Chelmsford, Mass.; George Duval, New Ipswich, N.H.; Dennis Goodine, Dracut, Mass.; James E. Lock, Newton, Mass.; Gerry Ouellette, Framingham, Mass.; Stanton B. Perry, Marblehead, Mass.; Maria Wagner, Groton, Mass.; Gregory R. Whittaker, Burlington, Mass.

[73] Assignee: C. R. Bard, Murray Hill, N.J.

[21] Appl. No.: 431,451

[22] Filed: May 1, 1995

Related U.S. Application Data

[60] Division of Ser. No. 49,162, Apr. 19, 1993, abandoned, which is a continuation-in-part of Ser. No. 824,019, Jan. 22, 1992, abandoned.

[51] Int. Cl.$^6$ .................................................. A61M 29/00
[52] U.S. Cl. .................................. 606/194; 623/11; 623/1
[58] Field of Search ........................ 606/191–194; 604/93, 96, 103, 264, 280; 623/1, 2, 11

[56] References Cited

U.S. PATENT DOCUMENTS

| 3,874,388 | 4/1975 | King et al. ............... 606/213 X |
| 4,503,569 | 3/1985 | Dotter ...................... 606/191 X |
| 4,699,611 | 10/1987 | Bunden ..................... 606/191 X |
| 4,733,665 | 3/1988 | Palmaz ..................... 606/191 X |
| 4,830,003 | 5/1989 | Wolff et al. .................. 606/191 |
| 4,878,906 | 11/1989 | Lindemann et al. ........ 606/155 X |
| 5,037,392 | 8/1991 | Hillstead .................... 606/194 X |
| 5,104,399 | 4/1992 | Lazarus ....................... 606/153 |
| 5,122,154 | 6/1992 | Rhodes ......................... 606/198 |
| 5,151,105 | 9/1992 | Kwan-Gett ................ 606/191 X |
| 5,156,620 | 10/1992 | Pigott ...................... 606/194 X |

FOREIGN PATENT DOCUMENTS

| 0304258 | 2/1989 | European Pat. Off. ............ 606/194 |

OTHER PUBLICATIONS

Front–Loading of Double–Umbrella Devices, a New Technique for Umbrella Delivery for Closing Cardiovascular Defects by Stanton B. Perry, M.D. and James E. Lock, M.D., *The Americal Journal of Cardiology*, vol. 70, Oct. 1, 1992, pp. 917–920.

*Primary Examiner*—Robert A. Clarke
*Attorney, Agent, or Firm*—Morgan & Finnegan, L.L.P.

[57] ABSTRACT

A system for percutaneous transluminal front-end delivery and retrieval of a collapsible prosthetic occluder includes a front-end loading portion, a control assembly and an introducer and retrieval sheath assembly. The front-end loading portion includes a tapering lumen portion and a smaller diameter distal lumen portion. An infusion port communicates with the distal lumen portion immediately adjacent the distal end of the tapering lumen portion. A valve assembly seals the front-end loading portion lumen proximally of the collapsed occluder. The distal end of the front-end loading portion lumen is inserted into the proximal end of an introducer and retrieval sheath assembly. A control assembly advances the occluder through the front-end loading portion, the introducer and retrieval sheath assembly and into the defect site. The retrieval sheath assembly is less flexible than the introducer sheath and is sufficiently rigid to evert the deployed occluder when retracted thereagainst.

92 Claims, 9 Drawing Sheets

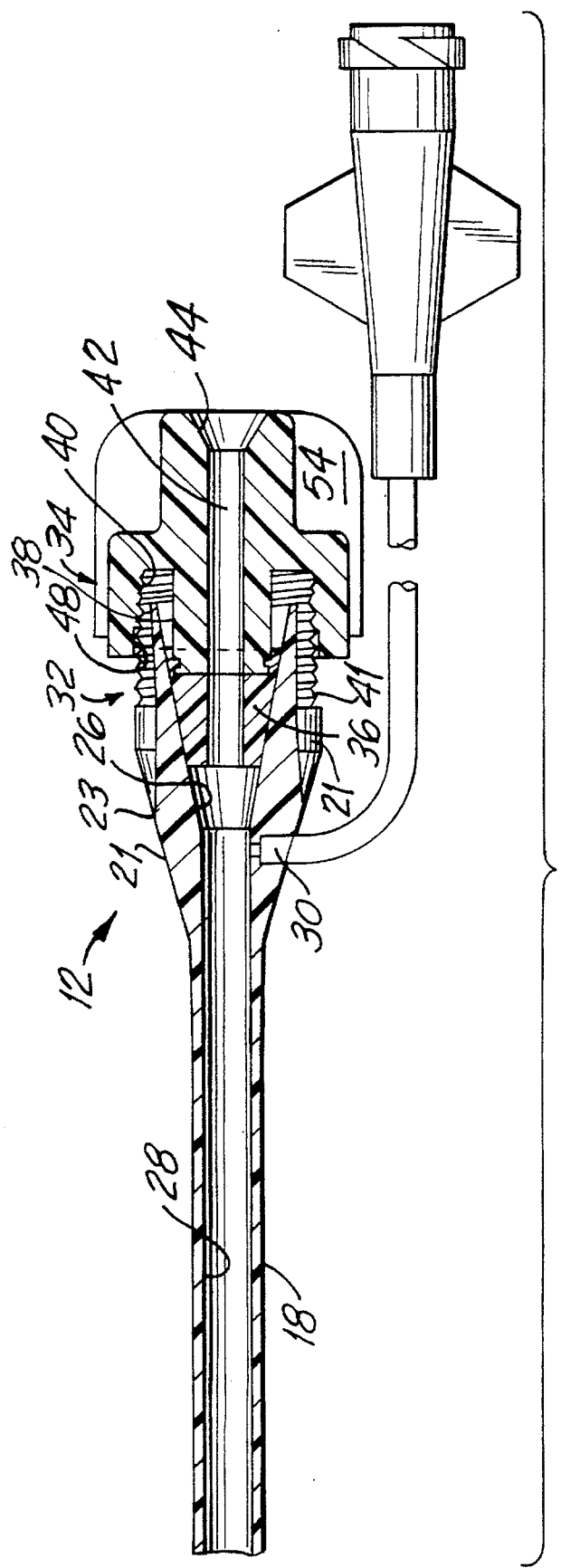
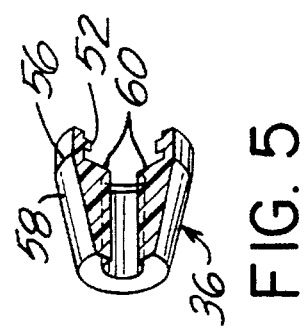
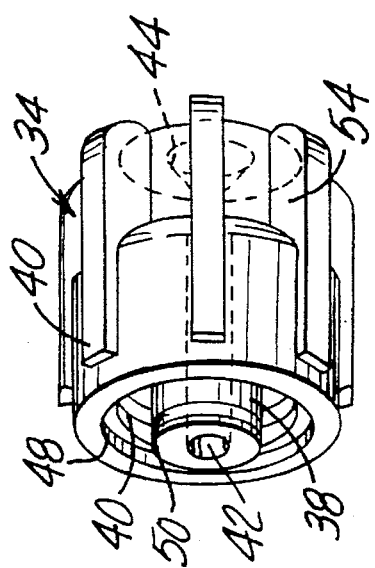
FIG. 3
FIG. 5
FIG. 4

SYSTEM FOR THE PERCUTANEOUS TRANSLUMINAL FRONT-END LOADING DELIVERY AND RETRIEVAL OF A PROSTHETIC OCCLUDER

This is a divisional application of U.S. patent application Ser. No. 08/049,162, filed Apr. 19, 1993, now abandoned, which is a continuation-in-part of U.S. patent application Ser. No. 07/824,019, filed Jan. 22, 1992, which is now abandoned.

FIELD OF INVENTION

The present invention relates to a system for the percutaneous transluminal front-end loading delivery and retrieval of a prosthetic occluder.

BACKGROUND OF THE INVENTION

Various prosthetic occluders for repairing intracardiac defects, such as interatrial and interventricular septal shunts, patent ductus arteriosus and aortic-pulmonary window have been proposed by the prior art. Representative is U.S. Pat. No. 3,874,388 to King et al. which discloses a device including a pair of opposed umbrella-like occluder elements which lock together at a central hub extending across the defect.

The King patent describes an assembly for percutaneous transluminal delivery of the umbrella-like occluder including a delivery cone, a catheter and an obturator guidewire. The distal end of the delivery cone is inserted in to the proximal end of the catheter and includes a cone-shaped lumen which compresses the occluder as it is advanced from the delivery cone to the catheter lumen in a procedure known as "front-end loading". The obturator guidewire extends through the delivery cone and the catheter lumen and is threaded at a distal tip to the occluder. Manipulation of the proximal end (outside of the patient) of the obturator wire reciprocally advances the collapsed umbrella-like occluder transluminally to the septal or ductus defect. Unscrewing the distal tip of the obturator wire, by rotating the proximal end, releases the deployed umbrella-like occluder from the delivery system.

A prosthetic occluder delivery system is described in W. J. Rashkind et al., "Non Surgical Closure of Patent Ductus Arterious: Clinical Application of the Rashkind PDA Occluder System," Circulation, Vol. 75, No. 3, March 1987, pg. 583–592. The Rashkind rear-end loading delivery system 500 illustrated in FIG. 1 includes a delivery assembly 501 and a separate loading device 502 for collapsing and then rear-end loading the collapsed occluder into the delivery assembly 501. The delivery assembly 501 includes an 85 cm long 8 French catheter 504, a delivery wire 506 and a locking wire 508. The distal tip of the catheter 504 includes a metal tubular pod 510 having a central lumen sized to maintain the occluder in the collapsed configuration. The delivery wire 506 and the locking wire 508 extend through the catheter 504 and beyond the pod 510. An attachment eye 512 extending from the occluder is seatable about a hemispherical-shaped knuckle 514 at the distal end of the locking wire 508. The lumen of a metal sleeve 516 at the distal end of the delivery wire 506 is sized to prevent the detaching of the knuckle 514 and attachment eye 512. The delivery wire 506 and locking wire 508 are axially moveable relative to one another and to the metal sleeve 516 by manipulation of a piston-cylinder control handle 518. A back bleed gasket assembly 520 at the proximal end of the catheter includes a side leg 522 for infusing liquid along the entire length of the catheter 504 and through the pod 510 to aspirate air bubbles from the compressed occluder.

The Rashkind procedure for loading the occluder, known as "rear-end loading", begins with the connection of the proximal occluder element 524 to the delivery assembly 501. The knuckle 514 is advanced distally of the metal sleeve 516 by closing the control handle 518. The attachment eye 512 is placed around the knuckle 514 so that the occluder elements 524, 526 are perpendicular to the longitudinal axis of the catheter 504. Extension of the control handle 518 draws the seated attachment eye 512 and knuckle 514 into the metal sleeve 516.

Tension applied to the sutures 528 extending through the loading device 502 causes the distal occluder element 524 to fold into the conical portion 530. As the sutures 528 are pulled through the loading device 502, the following proximal occluder element 26 folds backwards and is drawn into the conical portion 530. The occluder is pulled through the loading device 502 until it completely collapses in the distal portion 532. The pod 510 is advanced over the delivery wire 506 into the middle section 533 of the loading device 502. After cutting the sutures, the delivery wire is retracted which in turn draws the collapsed occluder completely into the pod 510. After removing the pod 510 from the loading device 502, the rear-end loaded collapsed occluder is flushed by infusing liquid from the side leg 522 all the way down the catheter 504 and through the pod 510. The flushed delivery assembly 501 is inserted into an already emplaced introducer sheath and then the pod 510 is transluminally advanced towards the defect.

The Rashkind rear-end loading system suffers from several deficiencies. It requires coordination of a separate loading cone and delivery assembly to collapse the occluder and then deliver the collapsed occluder into the introducer sheath. Handling of the lengthy and thick delivery catheter is awkward. Aspiration and flushing of the occluder has proved inefficient because the infusion fluid must be injected 85 cm downstream of the collapsed occluder. Mating of the attachment eye and knuckle, which is required to connect the occluder to the delivery system, requires a practiced skill and may take several attempts even for the experienced physician. Further, the rigidity of the metal pod precludes the delivery system from being navigated along the twisted curvature of the blood vessels adjacent the defect site and therefore prevents the delivery system from transporting the occluder to the defect site.

Accordingly, the prior art lacks a compact and efficient system for collapsing, flushing and then delivering a prosthetic occluder to a defect site.

SUMMARY OF THE INVENTION

The present invention is a system for percutaneous transluminal front-end loading delivery and retrieval of a prosthetic occluder used to repair congenital or acquired defects (shunts) in the heart or the major blood vessels thereof including interatrial and interventricular septal shunts, patent ductus arteriosus and aortic-pulmonary window. The percutaneous transluminal prosthetic occluder front-end loading delivery and retrieval system includes a front-end loading portion and a control assembly and an introducer and retrieval sheath assembly.

The front-end loading portion includes a conical-shaped lumen for collapsing the prosthetic occluder into a narrow or slender configuration which is advanceable through the lumen of the introducer sheath. A side leg having an infusion port provides direct access into the lumen to aspirate air bubbles from the compress occluder and a valve assembly seals the front-end loading portion from backflow of fluid. An elongated distal end of the front-end loading portion is inserted into a hub at the proximal end of the previously placed indwelling introducer sheath. The introducer sheath includes a flexible distal end which is bendable into a shape conforming to the curvature of the blood vessels adjacent the defect.

A control assembly guides the collapsed occluder from the front-end loading portion through the introducer sheath lumen and to the defect site. The control assembly includes a locking wire with a ball-head distal tip that is engageable with a ball-head tip of an extension arm of the collapsed occluder. An elongated tubular shaft surrounds the locking wire and includes a distal metal sleeve with an internally dimensioned lumen for holding the ball-head tips together, preventing disengagement of the control assembly and the occluder. Advancing the locking wire ball-head tip out of the metal sleeve releases a deployed occluder.

A retrieval sheath co-axially mounted about the introducer sheath includes a distal end which is less flexible than the distal end of the introducer sheath. A deployed but unreleased occluder may be retrieved by retracting the introducer sheath and control assembly against the distal end of the less flexible retrieval sheath until the expanded occluder everts into a narrow configuration withdrawable through the retrieval sheath lumen.

It is among the general objects of the invention to provide a front-end loading delivery device having a front-end loading portion for inserting a collapsible occluder into an introducer sheath.

It is a further object of the invention to provide a front-end loading delivery device having a front-end loading portion for enhancing removal of air bubbles from a collapsed occluder element.

It is a further object of the invention to provide a control assembly with a secure mechanism for releasably locking to an occluder.

An additional object of the invention is to provide an assembly for removing an expanded occluder without the necessity of surgical intervention.

Other objects and features of the present invention will become apparent from the following detailed description when taken in connection with the accompanying drawings which disclose multiple embodiments of the invention. It is to be understood that the drawings are designed for the purpose of illustration only and are not intended as a definition of the limits of the invention.

DESCRIPTION OF THE DRAWINGS

The foregoing and other objects and advantages of the invention will be appreciated more fully from the following drawings in which:

FIG. 3 is a sectional illustration of the front-end loading portion in accordance with the invention;

FIG. 4 is an illustration, partly in phantom, of the cap of the front-end loading portion illustrated in FIG. 3;

FIG. 5 is an illustration, partly in section, of the compressible gland of the front-end loading portion shown in FIG. 3;

DESCRIPTION OF THE PREFERRED EMBODIMENTS

Figure 1:
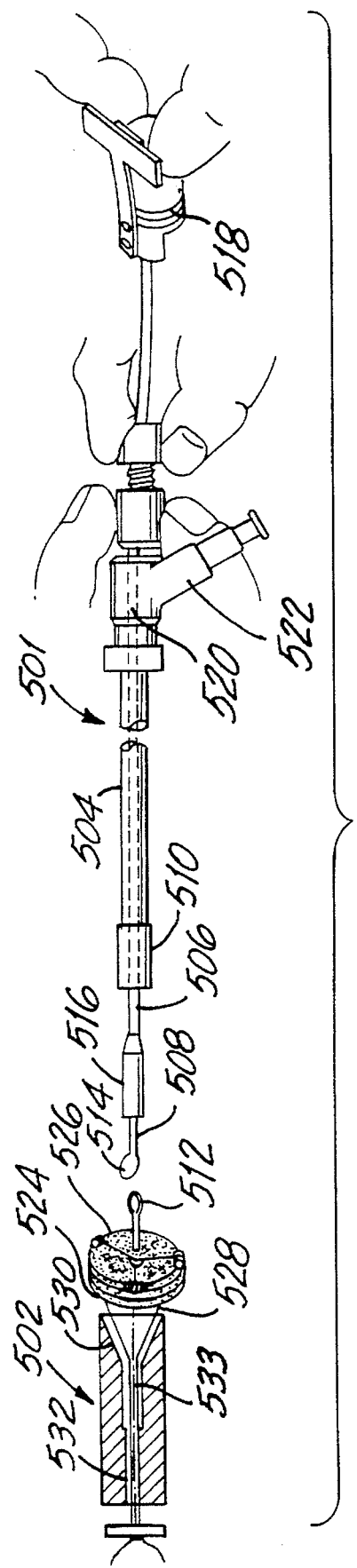
FIG. 1 is a fragmented illustration of the prior art Rashkind rear-end loading delivery system.
Figure 2:
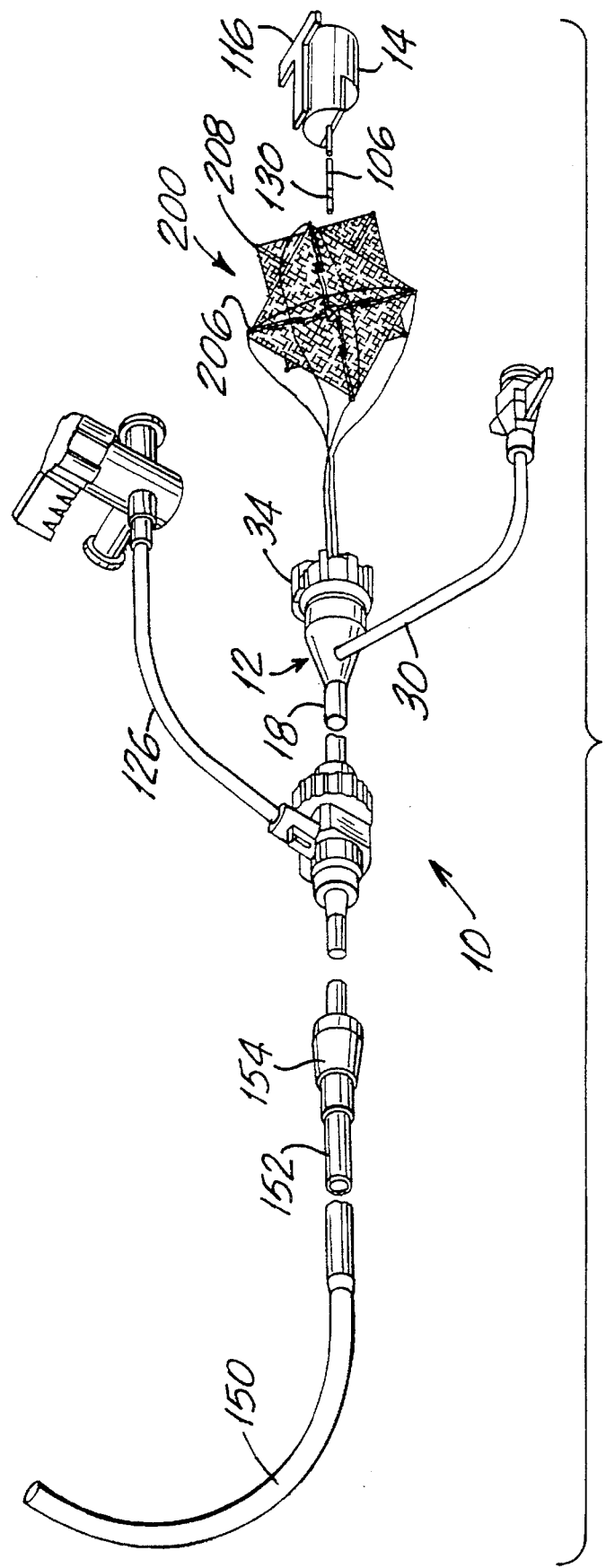
FIG. 2 is a fragmented illustration of the control assembly, front-end loading portion and introducer and retrieval sheath assembly in accordance with the invention.

The system for percutaneous transluminal front-end loading delivery and retrieval of a prosthetic occluder 10 shown in FIG. 2 includes a front-end loading portion 12, a control assembly 14, and an introducer and retrieval sheath assembly 16. The front-end loading portion 12 compresses the occluder into a narrow configuration which is suitable for loading into the lumen of the introducer and retrieval sheath assembly 16. After the occluder is collapsed, the distal end 18 of the front-end loading portion 12 is inserted into a hub at the proximal end of the previously placed indwelling introducer sheath. The proximal end of the control assembly 14 (outside of the patient) is manipulated to advance the occluder from the front-end loading portion 12 into and through the introducer and retrieval sheath assembly 16 until it reaches the defect site where it is deployed in an open configuration. Activation of the control assembly 14 then releases the deployed, fully expanded occluder.

The front-end loading portion 12 illustrated in FIGS. 3–5 includes a main body portion 21 having a tapering lumen portion 26, which preferably is conically shaped, and a uniform smaller diameter distal lumen portion 28 which is sized to compress the occluder to a predetermined diameter compatible with the introducer sheath lumen. A port 30 opens into the smaller diameter distal lumen portion 28 immediately adjacent the tapering distal portion 26. The port 30 is adapted to receive an infusion side leg or other structure for flushing saline or other fluids directly into the collapsed occluder to aspirate air bubbles therefrom. Preferably, the port 30 is positioned perpendicular to the longitudinal axis of the smaller diameter distal lumen portion 28 so that the infusion fluid is injected along a path perpendicular to the axis of the collapsed occluder.

A valve assembly 32 for sealing the lumen of the front-end loading portion 12 against backflow of the infusion fluid or blood is mounted to the proximal end of the main body portion 21. The valve assembly 32 includes a threaded cap 34 and a compressible gland 36. A shoulder or axial projection 38 compresses the gland when the threaded annular rim 40 of the cap 34 is tightened to the threaded portion 41 of the main tubular body 21. The cap 24 includes a locking step projection 48 which prevents the cap from separating from the main body portion 21 when the cap is loosened. The unscrewed cap can only be removed by pulling the cap until the locking step 48 resiliently snaps under the depending neck wall 49 at the proximal end of the main body 21. A ribbed surface portion 54 of the cap promotes gripping and rotating of the cap by the physician. The cap includes a central lumen 42 which is sized for slidable passage of the elongated shaft of the control assembly 14 A tapering proximal portion 44 of the cap lumen 42 facilitates insertion of the elongated shaft.

The compressible gland 36 includes a cylindrical portion 56 and a conical portion 58. The cylindrical portion 56 is attached to the cap 34 and includes an annular projection 52 which mates with an annular groove 50 in the cap shoulder 38. Alternatively, the annular projection may extend from the cap shoulder into an annular grove in the gland. The proximal wall 60 of the conical portion 58 resiliently seats against the cap shoulder and is the thrust bearing surface as the cap 34 is tightened. The shape of the conical portion 58, in the uncompressed state, closely matches the shape of the proximal end of the tapering lumen 26. The compressible gland 36 includes a central lumen 39 which in the non-compressed state has a diameter larger than the perimeter of the elongated shaft but smaller than the perimeter of the fully collapsed occluder. The assembled cap 34 and gland 36 define a continuous lumen 62 therethrough.

The cap and gland assembly is inserted into the proximal end of the main body portion 21 until the locking step resiliently snaps under the depending wall 49. Prior to tightening the cap 34, the conical portion 58 of the gland fills the proximal end of the tapering lumen 26. As the cap 34 is threaded to the main body portion 21, the gland 34 perimeter increasingly fills the unoccupied distal end of the tapering lumen 26 while the diameter of the gland lumen becomes increasingly smaller.

Preferable, the cap 34 and the tubular body 23 are formed of a rigid polycarbonate material which also is transparent so that the physician may observe the integrity of the prosthetic device during the loading procedure. Alternatively, the tubular body may be formed by insert molding the proximal end of a high density polyethylene tube having a uniform lumen diameter to a polycarbonate hub containing a tapering lumen. The gland 36 preferably is formed of a low durometer material such as a silicone or a latex.

In a representative embodiment, an 8 French front-end loading portion has a main body which is 2.345 inches long with the distal end being 1.522 inches long and the proximal section being 0.823 inches long. The tapering portion of the lumen has an inner diameter decreasing from 0.320 inches to 0.128 inches while the distal portion of the lumen has a uniform diameter of 0.128 inches. The distal end of the main body portion has an outside diameter of 0.122 inches. The infusion port is spaced slightly from the distal end of the tapering portion of the lumen and has an inner diameter of 0.07 inches that steps down to an inner diameter of 0.04 inches at the juncture with the distal lumen portion. The cap is 0.637 inches long with a through-lumen diameter of 0.09 inches. The compressible gland is 0.35 inches long with a lumen diameter in the non-compressed state of 0.08 inches.

Figure 6:
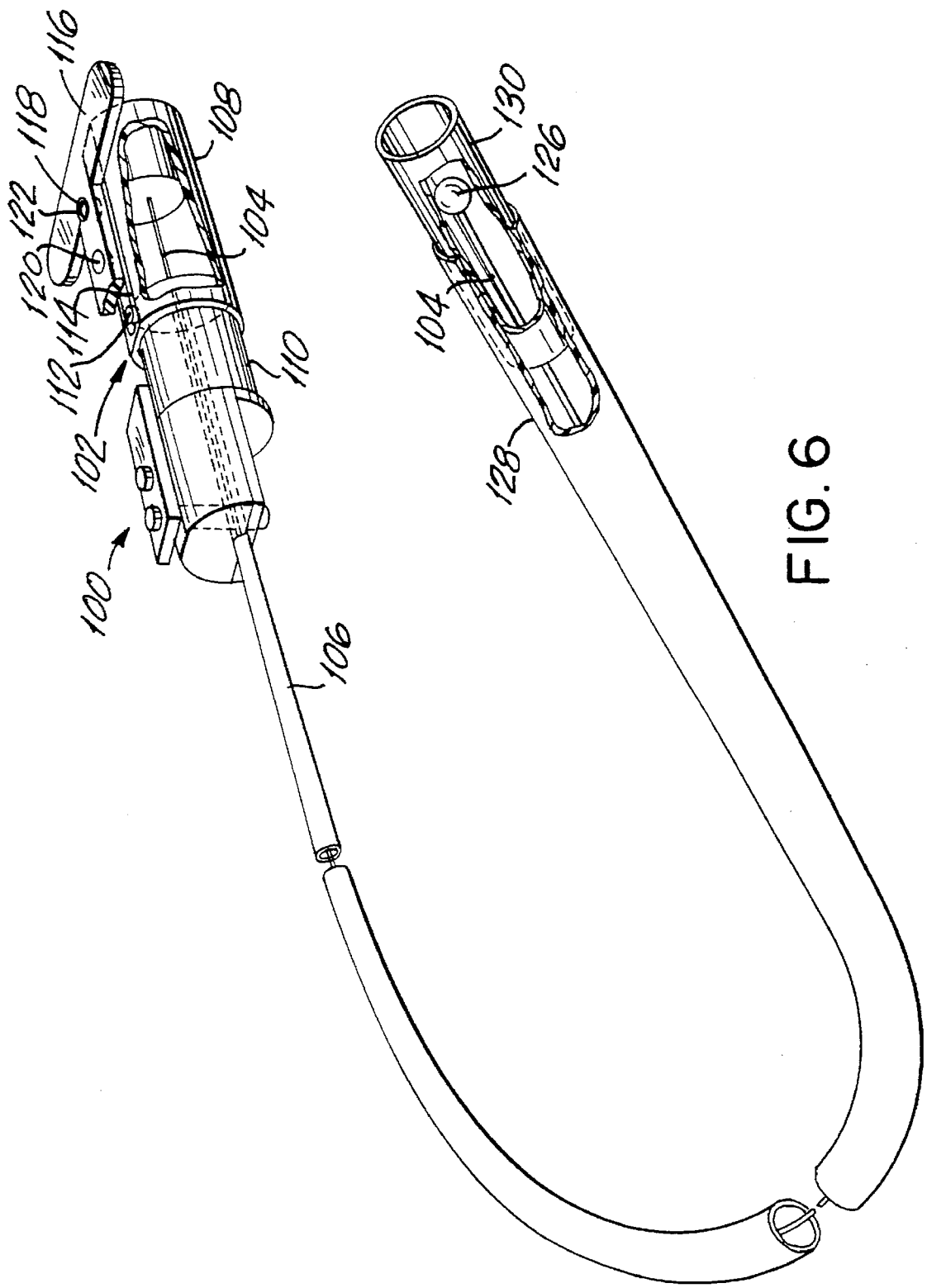
FIG. 6 is a fragmented illustration of the control assembly in accordance with the invention.

The control assembly 100 includes a plastic handle 102, a locking wire 104 and an elongated tubular shaft 106 as illustrated in FIG. 6. The handle 102 controls relative movement of the locking wire 104 controls relative movement of the locking wire 104 and the elongated shaft 106 and includes a telescopically arranged cylinder 108 and piston 110 formed of a polycarbonate material. The proximal end of the locking wire 104 preferably is fixed to the cylinder 108 by set screws or other means apparent to one of skill in the art while the proximal end of the elongated shaft 106 may be bonded to the piston 110 with an adhesive such as FDA-2 epoxy. The distal end of the locking wire includes a locking member that preferably is a spherical or ball-shaped enlargement 126 of the distal tip of the locking wire 104. The ball-head 126 may be formed by stamping or pressing the distal tip of the locking wire 104.

Alternatively, a separate bill-shaped member may be soldered, welded or brazed to the distal tip of the locking wire as would be apparent to those of skill in the art.

The elongated shaft 106 includes a hypodermic tube 107 and a non-thrombogenic plastic jacket 109 which encapsulates the hypodermic tube 107. The hypodermic tube 107 preferably is formed of type 304 stainless steel and the non-thrombogenic jacket preferably is formed of a polyurethane such as Pebax 7033 distributed by Atochem. The distal end of the jacket 109 extends beyond the distal tip of the hypodermic tube 107 to form a flexible distal segment 128 of the elongated shaft 106. The flexible distal segment 128 contains a less flexible member such as a small metal sleeve 130 which prevents the ball-head tip 126 and the ball-head end of the occluder extension arm from detaching as discussed below. When the ball-head tip 126 and the ball-head end have the same spherical shape and size, the small metal sleeve 130 has an inner diameter that ranges between the diameter of the spherical enlargement 126 and, preferable, is slightly smaller than twice the diameter of the spherical enlargement 126.

The telescoping arrangement of the cylinder 108 and piston 110 controls the relative position of the locking member and the metal sleeve. In the fully closed position of the handle 102, the spherical enlargement 126 extends beyond the small metal sleeve 130. In the retracted position, the spherical enlargement 126 is positioned within the small metal sleeve 130. A stop 112 extending from the piston 110 and an elongated groove 114 on the cylinder 108 cooperate to limit the extension of the handle 102. Respective apertures 120, 122 on a T-shaped plastic tab 116 are selectively engageable with a locking member 118 to secure the handle 102 in a retracted or a closed position.

In a representative embodiment, the hypodermic tube has a length of 45.01 inches with an inner diameter of 0.034 inches and an outer diameter of 0.048 inches. The non-thrombogenic plastic jacket portion encapsulating the hypodermic tube has an outer diameter of 0.064 inches while the flexible distal end has an outer diameter of 0.056 inches, an inner diameter of 0.048 and a length of 5.9 inches. The hypodermic tube and non-thrombogenic plastic jacket are joined by sliding an extruded plastic jacket over an FDA-2 epoxy adhesive coated hypodermic tube. The locking wire is formed of type 304 stainless steel and has a length of 45.6 inches and a diameter of 0.014 inches. The enlarged distal tip of the locking wire has a diameter of 0.025 inches. The distal metal sleeve has a lumen diameter of 0.040 inches and an outside diameter of 0.056 inches. A proximal extension of the distal metal sleeve has an outer diameter of 0.040 inches and a length of 0.025 inches. The proximal extension is coated with FDA-2 epoxy adhesive and inserted into the distal end of the non-thrombogenic plastic jacket to join the metal sleeve to the elongated shaft.

Figure 7:
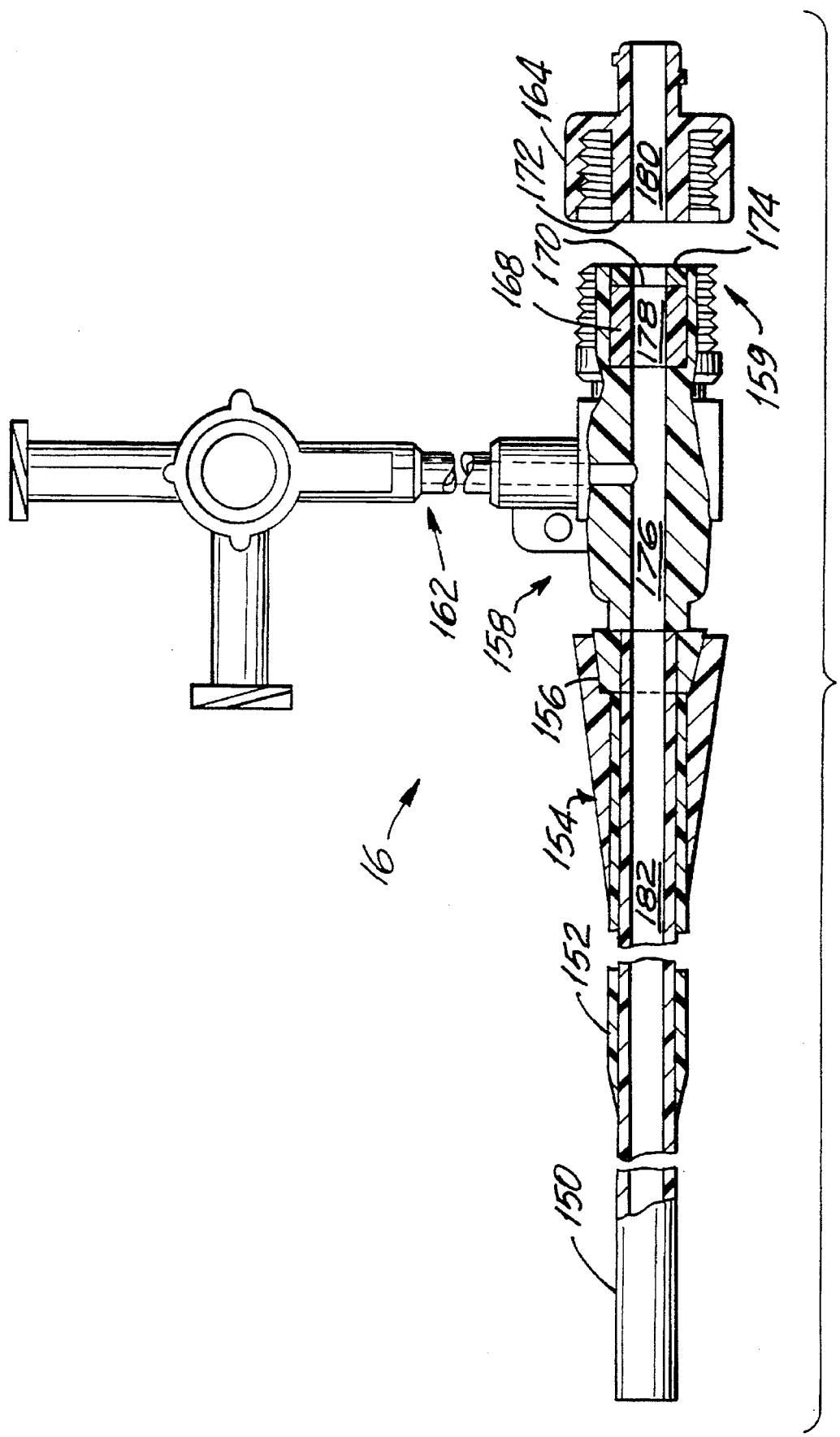
FIG. 7 is a fragmented illustration of the introducer and retrieval sheath assembly in accordance with the invention.

The introducer and retrieval sheath assembly 16 illustrated in FIG. 7 provides the transluminal pathway to the defect site for the occluder and includes a long flexible introducer sheath 150 and a shorter rigid retrieval sheath 152. The distal end of the introducer sheath is bendable into a shape that conforms with the vasculature adjacent the defect; for example, the curve of the pulmonary artery and the ductus when repairing a patent ductus arteriosus. The retrieval sheath 152 is less flexible than the distal portion of the introducer sheath 150 and is not similarly bendable. The introducer sheath 150 preferable is a single lumen tube with an inner lining of Teflon and an outer jacket formed of a polyurethane material such as Pebax 6333 distributed by Ato Chemical. The introducer sheath 150 preferably is formed by supporting a Teflon cylindrical liner on a mandrel and heat shrinking a polyurethane jacket thereover. A layer of FDA-2 epoxy adhesive may be interposed between the liner and the jacket to further secure the elements together. A process for surface treatment of the Teflon may be required to facilitate the bonding to the outer jacket. This may include molecular restructuring using plasma etching technologies or chemical treatment using etchants such as Tetra-Etch distributed by W. L. Gore & Associates, Inc. The mandrel preferably is curved at a distal tip to heat set the introducer sheath with a propensity for forming a curve similar to the curve of the body lumen adjacent the defect site. The retrieval sheath may be formed of a rigid polyurethane such as Isoplast 101 distributed by Dow Chemical.

A hub and flange assembly 151 releasibly connects the introducer and retrieval sheaths 150, 152. The polymeric cone-shaped flange 154 may be made of Kraton distributed by Shell Chemical Co. and preferably is bonded with FDA-2 epoxy adhesive at a distal end to the retrieval sheath 152 and is releasibly connected at a flexible proximal end to a less flexible tapering projection 156 of the hub 158. The cone-shaped flange 154 includes a lumen with a constant inner diameter distal portion and a flexible tapering proximal portion that is adapted to receive the less flexible tapering projection 156 in a tight fitting male/female relationship. The distal end of the hub 158 is insert molded to the proximal end of the introducer sheath 150.

A side leg 162 extending from the hub 158 is adapted to receive a syringe for flushing the introducer sheath. A valve 159 is connected to a proximal end of the hub 158 and includes a cap 164 and a compressible cylindrical-shaped gland 168 which seats within a valve chamber 170 within the hub 158. An axially projecting annular shoulder 172 compresses the gland 168 when the cap 164 is tightened to the hub 158. A Teflon washer 174 preferably is disposed between the proximal end of the gland 168 and the annular shoulder 172 and prevents rotation of the gland as the cap 164 tightens to the hub 158. The hub lumen 176, the gland 178 and the cap lumen 180 form a continuous passageway through the hub into the proximal end of the introducer sheath lumen and is sized to receive the distal end of the front-end loading delivery device.

In a representative embodiment an 8 French introducer sheath has an inner diameter of 0.108 inches, an outer diameter of 0.130 inches and a length of 33.46 inches. The retrieval sheath has an inner diameter of 0.158 inches, an outer diameter of 0.178 inches and a length of 7.87 inches. The cone-shaped flange is 1.120 inches long with an outside diameter that tapers from 0.415 inches to 0.240 inches. The tapering portion of the flange lumen ranges from 0.400 inches to 0.180 inches and has a length of 0.317 inches.

The loading and delivery of a prosthetic device is shown in FIGS. 8(a)–8(d). While the operation of the invention is discussed in connection with the repair of a patent ductus arteriosus, a similar loading and delivery procedure would be followed for the occlusion of arterial and septal defects. The prosthetic device 200 is a collapsible occluder, such as the occluder disclosed in the commonly assigned application for "Occluder and Method of Repair of Cardiac and Vascular Defects", Ser. No. 08/227,585, filed in the name of Dr. James E. Lock, George Duval and Rudy Davis, on Apr. 14, 1994, the entire disclosure of which is expressly incorporated by reference herein. A typical occluder has diametrically opposed umbrella-like elements which are connected in a face-to-face relationship by a central hub. The occluder framework can be collapsed and then automatically opened by resilient means which are provided in the elongated struts. A patch material is held in place by the strut framework and serves to cover and thereby occlude the shunt defect. At least one strut of the occluder element is provided with a radiopaque material to allow fluoroscopic visualization of the occluder during the catheterization procedure. Extending from the central hub through one of the occluder elements is an elongated locking arm which includes a ball-head 202 at its distal tip. The ball-head 202 preferably is approximately the same size and shape as the spherical enlargement 126 of the locking wire 104. Suture lines 204 connect the peripheral struts of the distal occluder element in parachute-like fashion so that the occluder can be drawn into the conical portion of the front-end loading portion 12.

Prior to insertion, the occluder 200 is soaked in normal saline. A syringe is used to flush further saline through the patch material to force air bubbles out through the occluder surface. The cap 34 and compressible gland 36 are threaded over the elongated shaft so that they are positioned proximally of the locking sleeve 130. The occluder 200 is secured to the control assembly 14 by inserting the ball-head end 202 of the extension arm into the metal sleeve 130 and retracting the piston-end of the handle so that the enlarged spherical projection 126 reciprocally moves into the sleeve 130 in abutting contact with the sleeve and the ball-head 202. The internal perimeter of the sleeve 130 prevents either of the ball-heads from escaping around the other. The T-shaped plastic tab is locked to the handle ensuring that the occluder is securely retained to the control assembly.

With one person holding the control assembly, another person draws the suture lines 204 through the lumen of the front-end loading portion 12 which in turn causes the distal occluder element 206 to collapse inwardly. The folded distal occluder element 200 is advanced through the conical lumen portion 26 and then is pulled into and through the smaller diameter lumen portion where it is tightly compressed. The proximal occluder element 208 is reciprocally advanced through the tapering lumen portion 26 until its legs fold rewardly. The suture lines 204 are pulled through the distal end of the front-end loading portion 12 until both occluder elements 206, 208 are tightly compressed within the uniform diameter distal portion 28 of the lumen. The sutures 204 are cut and removed from the distal occluder element 206 and then the cap 34 is tightened to the main body of the front-end loading portion so that the compressible gland 36 seals the tapering portion 26 of the front-end loading portion lumen about the elongated shaft. A syringe is attached to the side leg 30 and fluid, such as saline, is infused into the smaller diameter lumen 26 and into and across the collapsed prosthetic device to force any entrained air bubbles to exit through the distal portion of the lumen. Once sufficiently aspirated, the assembly is ready for insertion into the introducer sheath.

The introducer and retrieval sheath assembly previously has been placed in the patient following a standard right heart catheterization. Briefly, that procedure involves cannulating the right femoral vein with an 8 French introducer sheath and then manipulating a 7 French end hole angiocatheter through the right heart, the pulmonary artery, the ductus and into the descending aorta just distal to the ductus. An angiocardiogram may be performed to determine the ductus shape, size and anatomy. After the angiocardiogram, the angiocatheter is replaced with a 7F or 8F end hole catheter which is readvanced through the ductus and into the descending aorta. An exchange guidewire is passed through the catheter into the descending aorta. With a guidewire placed in the ductus, the end hole catheter is replaced with the introducer and retrieval sheath assembly which is advanced over the guidewire through the right heart, the pulmonary artery and ductus so that the tip of the assembly lies at the aortic end of the ductus. To facilitate steering and manipulation of the assembly, the flexible distal end of the introducer sheath may be pre-bent to conform to the curve of the pulmonary artery and ductus. The exchange guidewire, and dilator if used to predilate the vascular route, are removed and the introducer and retrieval assembly is flushed to eliminate air and any clots.

Figure 8A:
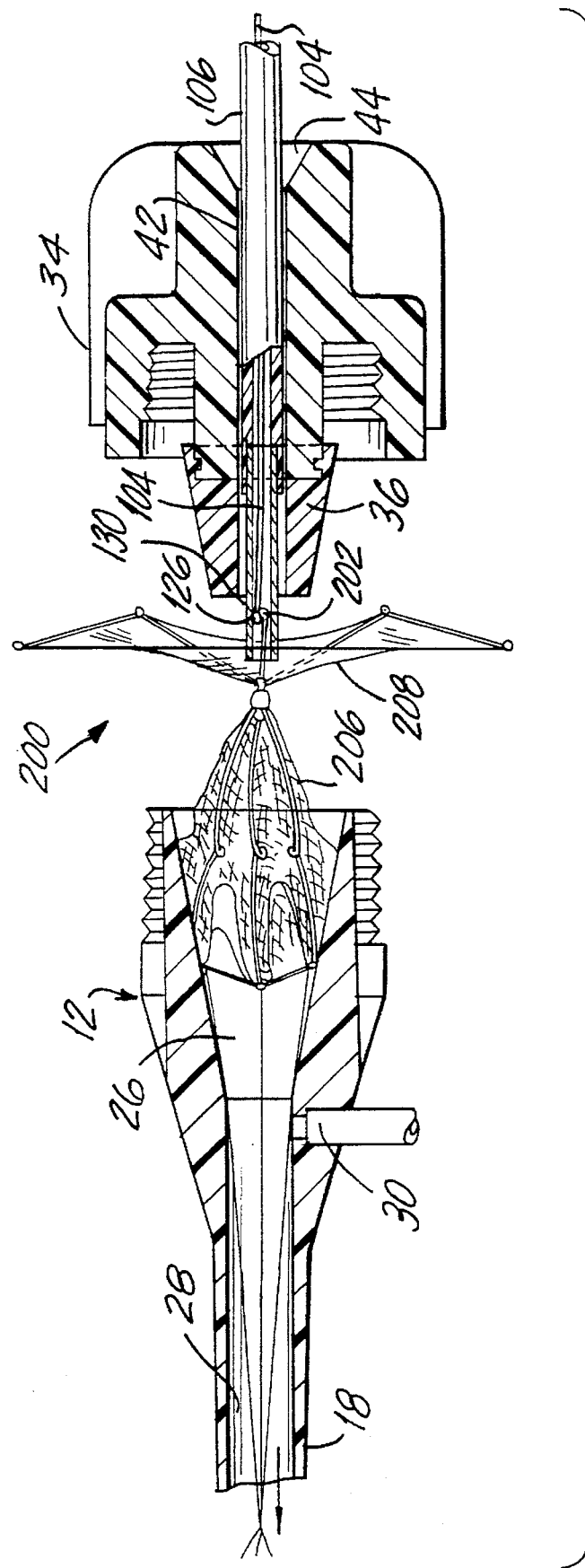
FIG. 8(a) is a sectional illustration of an occlusion device as it is being loaded into the front-end loading portion.
Figure 8B:
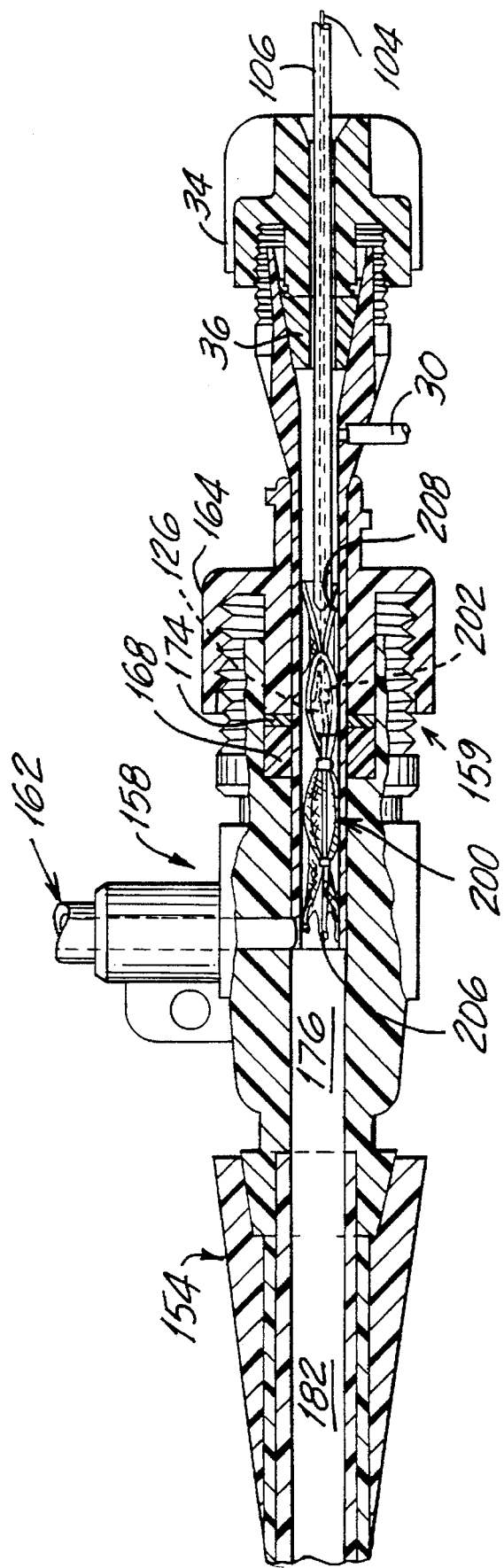
FIG. 8(b) is a sectional illustration of an occlusion device completely loaded in the front-end loading portion.

The distal end of the front-end loading portion 12 is inserted into the hub 158 which is attached to the proximal end of the introducer sheath 150 as illustrated in FIG. 8(b). The cap 164 is tightened to secure the front-end loading portion 12 to the introducer and retrieval sheath assembly 16. Forward movement of the control assembly (outside of the patient) advances the collapsed occluder 200 from the distal lumen portion of the front-end loading portion 12 into the introducer sheath lumen. At this time, the introducer sheath 150 may be flushed by infusing an appropriate solution through the side leg 162.

Figure 8C:
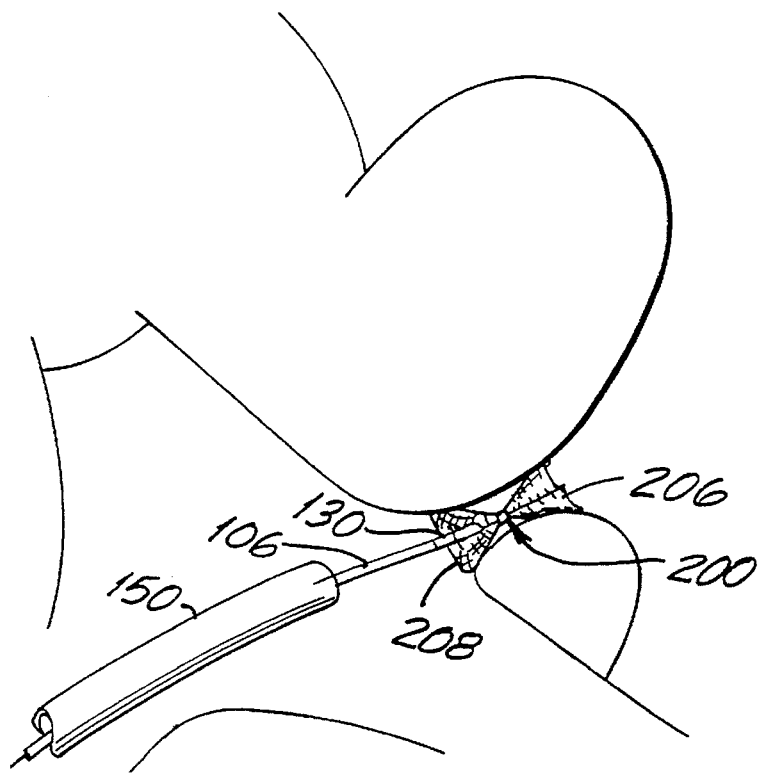
FIG. 8(c) is a schematic representation of all occlusion device being deployed within a defect with the occlusion device still attached to the control assembly.
Figure 8D:
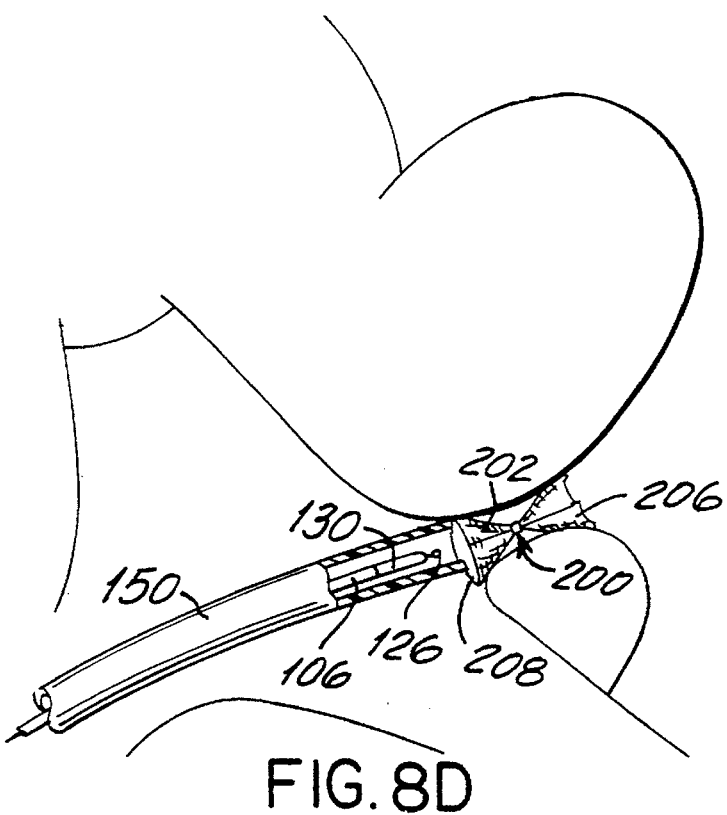
FIG. 8(d) is a schematic representation, partly in section, of the introducer sheath advanced to the occlusion device and the control assembly released from the occlusion device.

Using the patent ductus as an example of application, the control assembly is advanced slowly and carefully under fluoroscopy until the legs of the distal occluder element 206 spring open in the descending aorta as illustrated in FIG. 8(c). The control assembly and introducer sheath 150 are retracted together towards the ductus until the flexing of the distal legs and the conical end of the ductus is observed. While holding the control assembly, the introducer sheath 150 is withdrawn which allows the struts of the proximal occluder element 208 to spring open on the pulmonary side of the ductus. The introducer sheath 150 is readvanced against the proximal occluder element 208 to position the occluder 200. Closing the control handle advances the spherical enlargement 126 beyond the metal sleeve 130 and releases the ball-head locking member 202 of the deployed occluder 200 from the control assembly 13 as shown in FIG. 8(d). The control assembly may then be removed through the introducer sheath 150.

An angiocardiogram in the descending aorta adjacent to the ductus is performed ten to fifteen minutes after deployment to provide sufficient time for ingrowth of thrombus into the occluder. After determining that the placement and operation of the occluder is acceptable, the introducer and retrieval sheath assembly may be removed.

Figure 9:
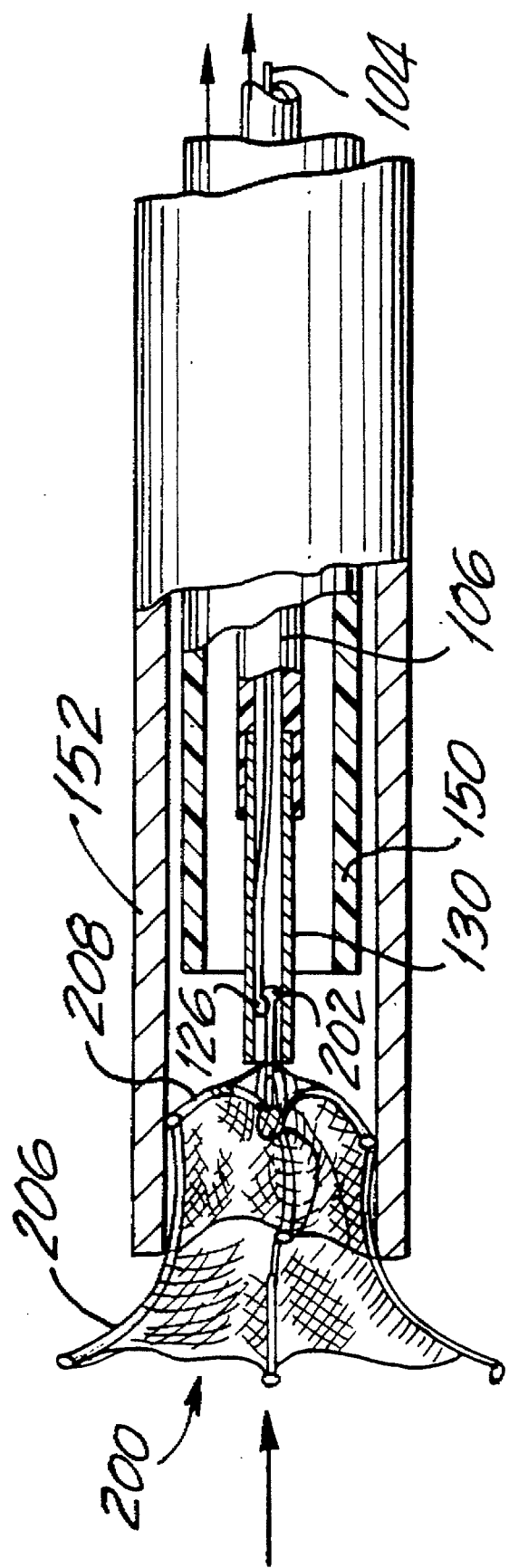
FIG. 9 is a schematic representation of a method of retrieving a deployed occlusion device in accordance with the invention.

In certain circumstances retrieval of an expanded, but not as yet released, occluder is required, such as when fluoroscopy reveals that the occluder is damaged or too small to seal the ductus defect. The flexible distal portion of the introducer sheath, which is bendable into a shape that approximates the pulmonary artery curve, is not rigid enough to provide a thrust bearing surface against which to overt the resiliently expanded occluder. Removal of the occluder is accomplished by withdrawing the introducer sheath 150 and the control assembly, which is still connected to the occluder, through the retrieval sheath until the expanded proximal occluder element 208 contacts the rigid distal tip of the retrieval sheath 152 as illustrated in FIG. 9. The repeated retraction of the introducer sheath 150 and the control assembly eventually everts the proximal occluder element 208. The collapsed proximal occluder element 208 then may be withdrawn into the retrieval sheath lumen. The distal occluder element 206, which naturally folds in the direction of the retrieval sheath, easily collapses into the retrieval sheath lumen as the control assembly and introducer sheath are further withdrawn.

The present invention therefore provides a system and method for percutaneous transluminal delivery and retrieval of a prosthetic occluder, amongst which are certain of the following advantages. The integral front-end loading portion facilitates collapsing of the occluder to a narrow configuration which may be flushed directly in the front-end loading portion and then delivered into the introducer sheath lumen. Connection of the occluder to the control assembly is reliably and quickly achieved by isolating compatible ball-head ends of the occluder and the locking wire within a narrowly dimensioned bore at the distal tip of the control wire. The present invention also permits the retrieval of an expanded but undeployed occluder, without surgical intervention. Retraction of the expanded occluder against the rigid distal tip of the retrieval sheath ultimately everts the occluder into a configuration which may be withdrawn through the retrieval sheath lumen.

It should be understood that the foregoing description of the invention is intended merely to be illustrative thereof and that other equivalents, embodiments and modifications of the invention may be apparent to those skilled in the art.

We claim:

1. A front-end loading delivery device for transluminal delivery of a collapsible prosthetic occluder and retrieval sheath assembly, comprising:
    a front-end loading portion comprising a main body having a distal end, a proximal end and a lumen extending therethrough, a portion of said lumen being tapered inwardly toward a smaller diameter distal portion;
    an infusion port extending through said main body and in direct communication with said distal portion of said lumen;
    a valve for sealing said lumen proximally of said small diameter distal portion;
    a control assembly comprising:
        an elongated shaft having a proximal end, a flexible distal end and a lumen extending therethrough;
        a locking wire extending through said lumen of said elongated shaft having a proximal end and a locking member at a distal end which is extendable beyond said flexible distal end of said elongated shaft; and
        a portion of said flexible distal end of said elongated shaft being adapted to lockingly hold said locking member and a locking member of a collapsible prosthetic occluder;
    an introducer sheath having a proximal end, a flexible distal end which is bendable to conform to a shape of a body lumen adjacent a defect site and a lumen extending therethrough; and
    a retrieval sheath removeably mounted about said introducer sheath and having a lumen extending therethrough adapted to slidably receive said introducer sheath, a distal end of said retrieval sheath being less flexible than said flexible distal end of said introducer sheath.

2. The front-end loading delivery and retrieval device according to claim 1 wherein said elongated shaft further comprises a hypodermic tube.

3. The front-end loading delivery and retrieval device according to claim 2 wherein said hypodermic tube is encapsulated in a non-thrombogenic jacket.

4. The front-end loading delivery and retrieval device according to claim 1 wherein said front-end loading portion distal end is constructed and arranged for insertion into a hub at a proximal end of said introducer sheath lumen.

5. The front-end loading delivery and retrieval device according to claim 1 wherein said infusion port opens into said front-end loading portion lumen distal portion immediately adjacent said inwardly tapered portion of said front-end loading portion lumen.

6. The front-end loading delivery and retrieval device according to claim 1 wherein said distal portion of said front-end loading portion lumen has a uniform diameter.

7. The front-end loading delivery device according to claim 1 wherein said front-end portion main body is transparent.

8. The front-end loading delivery and retrieval device according to claim 1 wherein said valve includes a compressible gland having a tapered outer portion constructed and arranged to closely fit in a non-compressed state within a proximal end of said tapered portion of said lumen.

9. The front-end loading delivery and retrieval device according to claim 8 wherein said compressible gland further includes a cylindrical portion proximally of said tapered portion.

10. The front-end loading delivery and retrieval device according to claim 1 wherein said valve includes a cap threadably mounted to said proximal end of said main body and having a lumen extending therethrough and a compressible gland having a lumen in alignment with said cap lumen.

11. The front-end loading delivery and retrieval device according to claim 10 wherein one of said cap and said gland has an annular groove and the other of said cap and said gland has an annular projection fitted within said groove.

12. The front-end loading delivery and retrieval device according to claim 10 wherein said cap is internally threaded.

13. The front-end loading delivery and retrieval device according to claim 12 wherein said cap includes a locking step projection distally of said internal threads.

14. The front-end loading delivery and retrieval device according to claim 10 wherein a perimeter of said cap lumen and said gland lumen in a non-compressed state are smaller than a perimeter of said collapsible prosthetic occluder in a collapsed state.

15. The front-end loading delivery and retrieval device according to claim 1 wherein said tapered portion of said front-end loading portion lumen is conically shaped.

16. The front-end loading delivery and retrieval device according to claim 1 wherein said front-end loading portion distal end is rigid.

17. The front-end loading delivery and retrieval device according to claim 1 wherein said portion of said control assembly flexible distal end includes a tip of said elongated shaft.

18. The front-end loading delivery and retrieval device according to claim 17 wherein said flexible distal end is formed of a plastic material and said tip is made of a metallic material.

19. The front-end loading delivery and retrieval device according to claim 18 wherein said tip is a metal sleeve.

20. The front-end loading delivery and retrieval device according to claim 19 wherein said locking member includes an enlarged spherical portion and said locking wire distal end and said metal sleeve has an inner diameter greater than the diameter of said enlarged spherical portion but less than twice the diameter of said enlarged spherical portion.

21. The front-end loading delivery and retrieval device according to claim 1 wherein an inner perimeter of a portion of said control assembly flexible distal end is adapted to lockingly hold said locking member and said locking member of the collapsible prosthetic occluder.

22. The front-end loading delivery and retrieval device according to claim 1 wherein said portion of said flexible distal end of said elongated shaft is less flexible than an adjacent portion of said flexible distal end.

23. The front-end loading delivery and retrieval device according to claim 1 wherein said locking members include an enlarged spherical portion of said distal end.

24. The front-end loading delivery and retrieval device according to claim 1 wherein said locking members are bulbous shaped.

25. The front-end loading delivery and retrieval device according to claim 1 wherein said control assembly comprises a handle connected to said proximal end of said elongated shaft and including a moveable member connected to said proximal end of said locking wire for reciprocally advancing and retracting said locking member relative to said portion of said flexible distal end of said shaft.

26. The front-end loading delivery and retrieval device according to claim 25 wherein said handle includes telescoping distal and proximal portions and a stop for limiting the displacement of said telescoping distal and proximal portions.

27. The front-end loading delivery and retrieval device according to claim 26 wherein said stop includes a groove extending through the surface of one of said telescoping distal and proximal portions and a projection extending into said groove from said other of said telescoping distal and proximal portions.

28. The front-end loading delivery and retrieval device according to claim 25 wherein said handle further includes means for releasably locking said telescoping distal and proximal portions relative to one another.

29. The front-end loading delivery and retrieval device according to claim 1 wherein said control assembly flexible distal end is bendable to conform to a shape of a body lumen adjacent to a defect site.

30. The front-end loading delivery and retrieval device according to claim 1, wherein a positioning wire is extendable through and beyond said introducer sheath lumen, having a distal tip connected to an article to be retrieved having a configuration larger than said introducer sheath lumen.

31. The front-end loading delivery and retrieval device according to claim 30 wherein said distal end of said removeably mounted retrieval sheath is positioned proximally of said flexible distal end of said introducer sheath.

32. The front-end loading delivery and retrieval device according to claim 30 wherein said removeably mounted retrieval sheath is moveable from a first position wherein said less flexible distal end of said removeably mounted retrieval sheath is proximal of said flexible distal end of said introducer sheath and said distal tip of said positioning wire to a second position wherein said less flexible distal end of said removeably mounted retrieval sheath is distal of said flexible distal end of said introducer sheath and said distal tip of said positioning wire.

33. The front-end loading delivery and retrieval device according to claim 30 further comprising a valve for sealing said proximal end of said lumen of said introducer sheath about said positioning wire.

34. The front-end loading delivery and retrieval device according to claim 30 further comprising a flange fixed to a proximal end of said removeably mounted retrieval sheath and having a lumen therethrough adapted to slidably receive said introducer sheath.

35. The front-end loading delivery and retrieval device according to claim 34 wherein said flange is tapered inwardly towards a distal tip thereof.

36. The front-end loading delivery and retrieval device according to claim 35 wherein said tapering flange is cone-shaped.

37. The front-end loading delivery and retrieval device according to claim 34 wherein said flange is releasably connected to a projection supported by a proximal end of said introducer sheath.

38. The front-end loading delivery and retrieval device according to claim 37 wherein said projection is tapered inwardly towards a distal tip thereof.

39. The front-end loading delivery and retrieval device according to claim 38 wherein said flange includes a proximal end adapted to receive said tapered projection in a releasable tight-fitting relationship.

40. The front-end loading delivery and retrieval device according to claim 39 wherein said proximal end of said flange is more flexible than said projection.

41. A percutaneous transluminal front-end loading delivery assembly, for delivery of a collapsible prosthetic occluder, and retrieval sheath assembly comprising:
   a front-end loading portion comprising a main body having a distal end, a proximal end and a lumen extending therethrough, a portion of said lumen being tapered inwardly toward a smaller diameter distal portion;
   an infusion port extending through said main body and in direct communication with said distal portion of said lumen, and a valve for sealing said lumen proximally of said small diameter distal portion;
   an introducer sheath having a flexible distal end, a proximal end and a lumen extending therethrough, said distal end of said front-end loading portion being removeably mountable to a hub at a proximal end of said introducer sheath;
   a retrieval sheath removeably mounted about said introducer sheath and having a lumen extending therethrough adapted to slidably receive said introducer sheath, a distal end of said retrieval sheath being less flexible than said flexible distal end of said introducer sheath; and
   a control assembly moveable through said lumen of said front-end loading portion and said lumen of said introducer sheath;
   said control assembly comprising;
      an elongated shaft having a proximal end, a flexible distal end and a lumen extending therethrough;
      a locking wire extending through said lumen of said elongated shaft having a proximal end and a locking member at a distal end which is extendable beyond said flexible distal end of said elongated shaft;
      a portion of said flexible distal end of said elongated shaft being adapted to lockingly hold said locking member and a locking member of the collapsible prosthetic occluder and a valve for sealing said proximal end of said introducer lumen about said distal end of said front-end loading portion.

42. The percutaneous transluminal front-end loading delivery and retrieval assembly according to claim 41 wherein said valve for sealing said introducer sheath lumen includes a cap threadably mounted to said introducer sheath, a compressible gland and a washer disposed between said cap and said compressible gland.

43. The percutaneous transluminal front-end loading delivery and retrieval system according to claim 41, wherein said elongated shaft further comprises a hypodermic tube.

44. The percutaneous transluminal front-end loading delivery and retrieval system according to claim 43 wherein said hypodermic tube is encapsulated in a non-thrombogenic jacket.

45. The percutaneous transluminal front-end loading delivery and retrieval system according to claim 41 wherein said front-end loading portion distal end is constructed and arranged for insertion into a hub at a proximal end of an introducer sheath lumen.

46. The percutaneous transluminal front-end loading delivery and retrieval system according to claim 41 wherein said infusion port opens into said front-end loading portion lumen distal portion immediately adjacent said inwardly tapered portion of said front-end loading portion lumen.

47. The percutaneous transluminal front-end loading delivery and retrieval system according to claim 41 wherein said front-end loading portion lumen has a uniform diameter.

48. The percutaneous transluminal front-end loading delivery and retrieval system according to claim 41 wherein said front-end loading portion main body is transparent.

49. The percutaneous transluminal front-end loading delivery and retrieval system according to claim 41 wherein said valve includes a compressible gland having a tapered outer portion constructed and arranged to closely fit in a non-compressed state within a proximal end of said tapered portion of said lumen.

50. The percutaneous transluminal front-end loading delivery and retrieval system according to claim 49 wherein said compressible gland further includes a cylindrical portion proximally of said tapered portion.

51. The percutaneous transluminal front-end loading delivery and retrieval system according to claim 41 wherein said valve includes a cap threadably mounted to said proximal end of said main body and having a lumen extending therethrough and a compressible gland having a lumen in alignment with said cap lumen.

52. The percutaneous transluminal front-end loading delivery and retrieval system according to claim 51 wherein one of said cap and said gland has an annular groove and the other of said cap and said gland has an annular projection fitted within said groove.

53. The percutaneous transluminal front-end loading delivery and retrieval system according to claim 51 wherein said cap is internally threaded.

54. The percutaneous transluminal front-end loading delivery and retrieval system according to claim 53 wherein said cap includes a locking step projection distally of said internal threads.

55. The percutaneous transluminal front-end loading delivery and retrieval system according to claim 51 wherein a perimeter of said cap lumen and said gland lumen in a non-compressed state are smaller than a perimeter of said collapsible prosthetic occluder in a collapsed state.

56. The percutaneous transluminal front-end loading delivery and retrieval system according to claim 41 wherein said tapered portion of said front-end loading portion lumen is conically shaped.

57. The percutaneous transluminal front-end loading delivery and retrieval system recited in claim 41 wherein said front-end loading portion distal end is rigid.

58. The percutaneous transluminal front-end loading delivery and retrieval system according to claim 41 wherein said portion of said control assembly flexible distal end includes a tip of said elongated shaft.

59. The percutaneous transluminal front-end loading delivery and retrieval system according to claim 41 wherein an inner perimeter of a portion of said control assembly flexible distal end is adapted to lockingly hold said locking member and said locking member of the collapsible prosthetic occluder.

60. The percutaneous transluminal front-end loading delivery and retrieval system according to claim 41 wherein said portion of said flexible distal end of said elongated shaft is less flexible than an adjacent portion of said flexible distal end.

61. The percutaneous transluminal front-end loading delivery and retrieval system according to claim 58 wherein said flexible distal end is formed of a plastic material and said tip is made of a metallic material.

62. The percutaneous transluminal front-end loading delivery and retrieval system according to claim 61 wherein said tip is a metal sleeve.

63. The percutaneous transluminal front-end loading delivery and retrieval system according to claim 62 wherein said locking member includes an enlarged spherical portion of said locking wire distal end and said metal sleeve has an inner diameter greater than the diameter of said enlarged spherical portion but less than twice the diameter of said enlarged spherical portion.

64. The percutaneous transluminal front-end loading delivery and retrieval system according to claim 41 wherein said locking members include an enlarged spherical portion of said distal end.

65. The percutaneous transluminal front-end loading delivery and retrieval system according to claim 41 wherein said locking members are bulbous shaped.

66. The percutaneous transluminal front-end loading delivery and retrieval system according to claim 41 wherein said control assembly comprises a handle connected to said proximal end of said elongated shaft and including a moveable member connected to said proximal end of said locking wire for reciprocally advancing and retracting said locking member relative to said portion of said flexible distal end of said shaft.

67. The percutaneous transluminal front-end loading delivery and retrieval system according to claim 66 wherein said handle includes telescoping distal and proximal portions and a stop for limiting the displacement of said telescoping distal and proximal portions.

68. The percutaneous transluminal front-end loading delivery and retrieval system according to claim 67 wherein said stop includes a groove extending through the surface of one of said telescoping distal and proximal portions and a projection extending into said groove from said other of said telescoping distal and proximal portions.

69. The percutaneous transluminal front-end loading delivery and retrieval system according to claim 66 wherein said handle further includes means for releasably locking said telescoping distal and proximal portions relative to one another.

70. The percutaneous transluminal front-end loading delivery and retrieval system according to claim 41 wherein said control assembly flexible distal end is bendable to conform to a shape of a body lumen adjacent to a defect site.

71. The percutaneous transluminal front-end loading delivery and retrieval system according to claim 41 wherein a positioning wire is extendable through and beyond said introducer sheath lumen, having a distal tip connected to an article to be retrieved having a configuration larger than said introducer sheath lumen.

72. The percutaneous transluminal front-end loading delivery and retrieval system according to claim 71 wherein said distal end of said removeably mounted retrieval sheath is positioned proximally of said flexible distal end of said introducer sheath.

73. The percutaneous transluminal front-end loading delivery and retrieval system according to claim 71 wherein said removeably mounted retrieval sheath is moveable from a first position wherein said less flexible distal end of said removeably mounted retrieval sheath is proximal of said flexible distal end of said introducer sheath and said distal tip of said positioning wire to a second position wherein said less flexible distal end of said removeably mounted retrieval sheath is distal of said flexible distal end of said introducer sheath and said distal tip of said positioning wire.

74. The percutaneous transluminal front-end loading delivery and retrieval system according to claim 71 further comprising a valve for sealing said proximal end of said lumen of said introducer sheath about said positioning wire.

75. The percutaneous transluminal front-end loading delivery and retrieval system according to claim 71 further comprising a flange fixed to a proximal end of said removeably mounted retrieval sheath and having a lumen therethrough adapted to slidably receive said introducer sheath.

76. The percutaneous transluminal front-end loading delivery and retrieval system according to claim 75 wherein said flange is tapered inwardly towards a distal tip thereof.

77. The percutaneous transluminal front-end loading delivery and retrieval system according to claim 76 wherein said tapering flange is cone-shaped.

78. The percutaneous transluminal front-end loading delivery and retrieval system according to claim 75 wherein said flange is releasably connected to a projection supported by a proximal end of said introducer sheath.

79. The percutaneous transluminal front-end loading delivery and retrieval system according to claim 78 wherein said projection is tapered inwardly towards a distal tip thereof.

80. The percutaneous transluminal front-end loading delivery and retrieval system according to claim 79 wherein said flange includes a proximal end adapted to receive said tapered projection in a releasable tight-fitting relationship.

81. The percutaneous transluminal front-end loading delivery and retrieval system according to claim 80 wherein said proximal end of said flange is more flexible than said projection.

82. A percutaneous transluminal introducer and retrieval sheath assembly, comprising:

an introducer sheath having a proximal end, a flexible distal end which is bendable to conform to a shape of a body lumen adjacent a defect site and a lumen extending therethrough;

a retrieval sheath removeably mounted about said introducer sheath and having a lumen extending therethrough adapted to slidably receive said introducer sheath, a distal end of said retrieval sheath being less flexible than said flexible distal end of said introducer sheath; and a control assembly comprising:
an elongated shaft having a proximal end, a flexible distal end and a lumen extending therethrough;
a locking wire extending through said lumen of said elongated shaft having a proximal end and a locking member at a distal end which is extendable beyond said flexible distal end of said elongated shaft;
said locking wire extending through and beyond said introducer sheath lumen, and having said distal locking member connected to an article to be retrieved having a configuration larger than said introducer sheath lumen.

83. The percutaneous transluminal introducer and retrieval assembly according to claim 82 wherein said distal end of said removeably mounted retrieval sheath is positioned proximally of said flexible distal end of said introducer sheath.

84. The percutaneous transluminal introducer and retrieval assembly according to claim 82 wherein said removeably mounted retrieval sheath is moveable from a first position wherein said less flexible distal end of said removeably mounted retrieval sheath is proximal of said flexible distal end of said introducer sheath and said distal locking member of said locking wire to a second position wherein said less flexible distal end of said removeably mounted retrieval sheath is distal of said flexible distal end of said introducer sheath and said distal locking member of said locking wire.

85. The percutaneous transluminal introducer and retrieval assembly according to claim 82 further comprising a valve for sealing said proximal end of said lumen of said introducer sheath about said locking wire.

86. The percutaneous transluminal introducer and retrieval assembly according to claim 82 further comprising a flange fixed to a proximal end of said removeably mounted retrieval sheath and having a lumen therethrough adapted to slidably receive said introducer sheath.

87. The percutaneous transluminal introducer and retrieval assembly according to claim 86 wherein said flange is tapered inwardly towards a distal tip thereof.

88. The percutaneous transluminal introducer and retrieval assembly according to claim 87 wherein said tapering flange is cone-shaped.

89. The percutaneous transluminal introducer and retrieval assembly according to claim 86 wherein said flange is releasably connected to a projection supported by a proximal end of said introducer sheath.

90. The percutaneous transluminal introducer and retrieval assembly according to claim 89 wherein said projection is tapered inwardly towards a distal tip thereof.

91. The percutaneous transluminal introducer and retrieval assembly according to claim 90 wherein said flange includes a proximal end adapted to receive said tapered projection in a releasable tight-fitting relationship.

92. The percutaneous transluminal introducer and retrieval assembly according to claim 91 wherein said proximal end of said flange is more flexible than said projection.

\* \* \* \* \*